United States Patent [19]
De Simone

[11] Patent Number: 6,037,373
[45] Date of Patent: Mar. 14, 2000

[54] USE OF L-ACETYLCARNITINE, L-ISOVALERYLCARNITINE, L-PROPIONYLCARNITINE FOR INCREASING THE LEVELS OF IGF-1

[75] Inventor: Claudio De Simone, Ardea RM, Italy

[73] Assignees: SIGMA-TAU Industrie Farmaceutiche Riunite S.p.A.; MENDES s.r.l., both of Roma, Italy

[21] Appl. No.: 09/147,465

[22] PCT Filed: May 15, 1997

[86] PCT No.: PCT/IT97/00113

§ 371 Date: Jan. 4, 1999

§ 102(e) Date: Jan. 4, 1999

[87] PCT Pub. No.: WO98/01128

PCT Pub. Date: Jan. 15, 1998

[30] Foreign Application Priority Data

Jul. 5, 1996 [IT] Italy ................................ RM96A0479

[51] Int. Cl.⁷ .................................................. A61K 31/205
[52] U.S. Cl. .............................................................. 514/556
[58] Field of Search ............................................. 514/556

[56] References Cited

U.S. PATENT DOCUMENTS

| | | | |
|---|---|---|---|
| 5,227,518 | 7/1993 | Cavazza .................................. | 560/253 |
| 5,240,961 | 8/1993 | Shug ....................................... | 514/556 |
| 5,656,628 | 8/1997 | Weil et al. ............................ | 514/228.8 |

FOREIGN PATENT DOCUMENTS

| | | |
|---|---|---|
| 0 516 594 | 12/1992 | European Pat. Off. . |
| WO 94/01101 | 1/1994 | WIPO . |
| WO 95/00137 | 1/1995 | WIPO . |

OTHER PUBLICATIONS

W.G. Sannita, et al., Documenta Ophthalmologica, vol. 70, pp. 89–96, "Effects of Intravenous L-acetylcarnitine on Retinal Oscillatory Potentials", 1988.

D.J. Paulson, et al., Cardiovascular Research, vol. 20, No. 79 pp. 536–541, "Protection of the Ischaemic Myocardium by L-propionylcarnitine: Effects on the Recovery of Cardiac Output After Ischaemia and Reperfusion, Carnitine Transport, and Fatty Acid Oxidation", 1986.

A.J. Liedtke, et al., American Journal of Physiology, vol. 255, No. 1, Pt. 2, pp. H169–H176, "Effects of L-propionylcarnitine on Mechanical Recovery During Reflow in Intact Hearts", 1988.

C. Adembri, et al., Histology and Histopathology, vol. 9, No. 4, pp. 683–690, "Ischemia-Reperfusion of Human Skeletal Muscle During Aortiliac Surgery: Effects of Acetylcarnitine", 1994.

J.A. Leipälä, et al., Journal of Applied Physiology, vol. 71, No. 4, pp. 1518–1522, "Protection of the Reperfused Heart by L-propionylcarnitine", 1991.

*Primary Examiner*—Raymond Henley, III
*Attorney, Agent, or Firm*—Oblon, Spivak, McClelland, Maier & Neustadt, P.C.

[57] ABSTRACT

A method is provided for increasing the levels of IGF-1 for the therapeutic treatment or prophylaxis of cytological disorders or diseases related to IGF-1 selected from the group consisting of neuropathies of the optic nerve and of the olfactory nerve, neuralgia of the trigeminal nerve, Bell's paralysis, amyotrophic lateral sclerosis, osteoporosis, arthropathy, arthritis, cervical spondylosis and hernia of the intervertebral discs, clinical syndromes of reduced height, cachexia and acute or chronic hepatic necrosis, Turner's syndrome, sarcopoenia, growth hormone insensitivity syndromes, obesity, asthenia, myasthenia and heart asthenia, immunodeficiencies and reperfusion injuries, and for the cicatrization of wounds, the healing of ulcers, the treatment of burns, tissue regeneration, cutaneous, intestinal and hepatic tissue regeneration and the formation of dentine, that includes administering, to a patient in need thereof, at least one selected from the group consisting of L-acetylcarnitine, L-isovalerylcarnitine, and L-propionylcarnitine or pharmacologically acceptable salts thereof.

11 Claims, No Drawings

USE OF L-ACETYLCARNITINE, L-ISOVALERYLCARNITINE, L-PROPIONYLCARNITINE FOR INCREASING THE LEVELS OF IGF-1

This is a 371 of PCT/IT97/00113 filed May 15, 1997.

The present invention relates to a novel therapeutic use of L-acetylcarnitine, L-isovalerylcarnitine, L-propionylcarnitine or pharmacologically acceptable salts thereof for increasing the levels of IGF-1 (insulin-like growth factor 1) for the therapeutic treatment or prophylaxis of cytological disorders or diseases related to IGF-1. More particularly, the present invention relates to the use of L-acetylcarnitine, L-isovalerylcarnitine, L-propionylcarnitine or pharmacologically acceptable salts thereof for the therapeutic treatment or prophylaxis of individuals in whom IGF-1 contributes towards the pathogenesis of a particular disease or provokes cytological disorders.

Like other growth factors, IGF-1 promotes cell growth and differentiation. The administration of IGF-1 obtained as a protein purified by molecular biology methods has made it possible to confirm the effects observed in vitro with cells, on animal models and in man. Essentially, the action of IGF-1 is similar to that of insulin, that is to say an increase in the uptake of glucose, a reduction in ketones and fatty acids in the serum and an increase in protein synthesis. In accordance with these and other metabolic effects, clinical studies have been undertaken in order to evaluate the efficacy of IGF-1 in a range of diseases. IGF-1 has been administered to patients with type-II diabetes, to cachectic patients, to patients with ischemic damage at the neuronal, myocardial or renal level, and has been proposed for repairing and regenerating tissues (W.L. Lowe, Insulin-like growth factors, Scientific American Science and Medicine p. 62, March 1996).

From the above, it is clear that the administration of IGF-1 may be therapeutically useful in various morbid conditions. Examples of diseases or disorders which may be prevented, cured or improved by the administration of IGF-1 include neuropathies of the optic nerve and of the olfactory nerve, neuralgia of the trigeminal nerve, Bell's paralysis, amyotrophic lateral sclerosis and other motor neuron diseases, degeneration of the retina, osteoporosis, arthropathy, arthritis, cervical spondylosis and hernia of the intervertebral discs, clinical syndromes of reduced height, cachexia, acute or chronic hepatic necrosis, Turner's syndrome, sarcopoenia, growth hormone insensitivity syndromes, diabetes, obesity, asthenia in general and in particular myasthenia and heart asthenia, immunodeficiencies and reperfusion injuries. IGF-1 moreover appears to be useful for the cicatrization of wounds, the healing of ulcers, the treatment of burns, tissue regeneration in general and in particular that of cutaneous, intestinal and hepatic tissue, and the formation of dentine.

Unfortunately, the administration of IGF-1 in man brings about undesirable effects such as oedema, pain in the temporomandibular joint and arthralgia. These symptoms are such as to prevent the administration of IGF-1 from being recommended or are responsible for interrupting the treatment. It is therefore necessary to find novel substances which are capable of inducing the production of IGF-1.

According to the present invention, the administration of L-acetylcarnitine, L-isovalerylcarnitine, L-propionylcarnitine or pharmacologically acceptable salts thereof is capable of inducing the production of IGF-1 without the undesirable effects produced by the administration of exogenous IGF-1.

In the description which follows, the expression pharmacologically acceptable salt of L-acetylcarnitine, of L-isovalerylcannitine or of L-propionylcarnitine is understood to refer to any salt of the above with an acid which does not give rise to undesirable toxicity or side-effects. Such acids are well known to pharmacologists and to experts in the pharmaceutical field.

Non-limiting examples of such salts are: chloride; bromide; iodide; aspartate, in particular hydrogen aspartate; citrate, in particular hydrogen citrate; tartrate; phosphate, in particular hydrogen phosphate; fumarate, in particular hydrogen fumarate; glycero-phosphate, glucose phosphate; lactate; maleate, im parcular hydrogen rnaleate; orotate; oxalate, in particular hydrogen oxalate; sulphate, in particular hydrogen sulphate; tricbloroacetate, trifluoroacetate and methanesulphonate.

In the description which follows, for the purposes of brevity and for ease of explanation, reference will be made only to L-acetylcarnitine, it being understood that the description given applies also to the above-mentioned L-isovalerylcarnitine and L-propionylcarnitine and to pharmacologically acceptable salts thereof.

Therapeutic uses of L-acetylcaritine, L-isovalexycarniine and L-propionylcarnitine for the therapeutic treatment of myocardial arrhythmia and ischemia, peripheral functiona vasculopathy of the arteries, senile dementia, peripheral neuropathies and myopathies are already previously known. For instance, EP 0 516 594 Al discloses the use of propionyl- and isovaleryl L-carnitine for treating myopathies, neuronal degeneration and for inhibiting proteolysis. Cardiov. Res. 1986, 20:536–541 deals with the protection of the ischaemic myocardium by propionyl L-carnitine. Docum. Ophtal. 1988, 70:89–96 hints at therapeutic potentialities of acetyl L-carnitine in diabetes and diabetic complications of the visual system. For instance, EP 0516594 A1 discloses the use of propionyl- and isovaeeryl L-carpitive for treating myopather, neuronal degeneration and for inhibiting proteolyses. Carticv Res. 1986, 20. 536–547 declr with protection of the ischamic myolanlium by propionyl L-carnistive. Docum. Ophthal. 1988, 70, 84–96 hints at therapeutic potential thereof acetyl L-lzrutive complications of the visual system. However, there is no correlation between these known therapeutic uses and the subject of the present invention.

It has now been found, surprisingly, that L-acetylcanitie, L-iso-valerylcarnitine, L-propionylcarnitine or pharmaceutically acceptable salts thereof are capable of increasing the levels of IGF-1 in human biological fluids. It should be emphasized that, on the bums of extensive supporting scientific literature, the mechanism of action of L-acetylcarnitine has been focused at the metabolic level, more specifically demonstrating a protective action with respect to the mitochondcria, whereas the present invention demonstrates an action mediated by the production of IGF-1.

In one embodiment of the present invention, the L-acetylcamiie, L-isovalerylcarnitine, L-propionylcarnitine or pharmaceutically acceptable salts thereof are administered in combination with vasodilatory, vascular, endocrinological, immunological, cytostatic, immunomodulatory, anti-inrlammatory or cortisone pharmaceutical products, IGF-1, IGF-1 binding proteins, growth hormones and other cell growth factors such as, for example, epidermal growth factor, and erythropoietin.

The examples which follow are for the purpose of illustrating the invention and should in no way be understood as implying a limitation in the scope thereof.

EXAMPLE 1

13 individuals infected with HIV were enroled. Blood was taken before and after treatment with L-acetylcarnitine orally at a dosage of 3 g/day for 8 weeks. The levels of IGF-1 were measured using a kit supplied by Amersham Italia s.r.l., Milan, and the results were expressed as ng of IGF-1/100 µl of serum.

TABLE 1

| Patient # | Before | After |
|---|---|---|
| 1 | 0.03 | 4.16 |
| 2 | 0.03 | 5 |
| 3 | 0.03 | 0.06 |
| 4 | 0.02 | 5 |
| 5 | 0.02 | 0.05 |
| 6 | 0.04 | 3.25 |
| 7 | 0.25 | 5 |
| 8 | 0.02 | 0.03 |
| 9 | 0.1 | 5 |
| 10 | 0.07 | 5 |
| 11 | 0.03 | 5 |
| 12 | 0.16 | 3.49 |
| 13 | 0.03 | 0.18 |
| AVERAGE | 0.06 | 3.17 |
| Standard deviation | 0.07 | 2.22 |
| Standard error | 0.02 | 0.62 |
| Student test | | 0.0002 |

It is known that individuals infected with HIV can have variable levels of IGF-1 in their serum. The experiments reported here demonstrated that the oral administration of L-acetylcarnitine increases the levels of IGF-1in peripheral blood.

EXAMPLE 2

Four patients aged above 70 and with healthy dispositions were treated with 2 grams/day of L-acetylcarnitine parenterally for 7 days. The results of the doses of IGF-1 before and after the treatment are reported in Table 2.

TABLE 2

| Patient # | Before | After |
|---|---|---|
| 1 | 0.01 | 2.1 |
| 2 | 0.02 | 3.6 |
| 3 | 0.05 | 1.8 |
| 4 | 0.03 | 3.8 |
| AVERAGE | 0.03 | 2.83 |
| Standard deviation | 0.02 | 1.02 |
| Standard error | 0.008 | 0.51 |
| Student test | | 0.01 |

I claim:

1. A method for increasing the levels of IGF-1 for the therapeutic treatment or prophylaxis of cytological disorders or diseases related to IGF-1 selected from the group consisting of neuropathies of the optic nerve and of the olfactory nerve, neuralgia of the trigeminal nerve, Bell's paralysis, amyotrophic lateral sclerosis, osteoporosis, arthropathy, arthritis, cervical spondylosis and hernia of the intervertebral discs, clinical syndromes of reduced height, cachexia and acute or chronic hepatic necrosis, Turner's syndrome, sarcopoenia, growth hormone insensitivity syndromes, obesity, asthenia, myasthenia and heart asthenia, immunodeficiencies and reperfusion injuries, and for the cicatization of wounds, the healing of ulcers, the treatment of burns, tissue regeneration, cutaneous, intestinal and hepatic tissue regeneration and the formation of dentine, comprising:

administering, to a patient in need thereof, at least one selected from the group consisting of L-acetylcarnitine, L-isovalerylcarnitine, and L-propionylcarnitine or pharmacologically acceptable salts thereof.

2. The method of claim 1, in which the L-acetylcarnitine, L-isovalerylcarnitine, L-propionylcarnitine or pharmacologically acceptable salts thereof are administered in combination with at least one selected from the group consisting of vasodilatory, vascular, endocrinological, immunological, cytostatic, immunomodulatory, anti-inflammatory or cortisone pharmaceutical products, IGF-1, IGF-I binding proteins, growth hormones, epidermal growth factor, and erythropoietin.

3. The method of claim 1, in which L-acetylcarnitine is administered.

4. The method of claim 1, in which L-isovalerylcarnitine is administered.

5. The method of claim 1, in which L-propionylcarnitine is administered.

6. The method of claim 3, wherein 0.01 mg-15 g per day of L-acetylcarnitine are administered.

7. The method of claim 3, wherein 0.1 mg-10 g per day of L-acetylcarnitine are administered.

8. The method of claim 4, wherein 0.01 mg-15 g per day of L-isovalerylcarnitine are administered.

9. The method of claim 4, wherein 0.1 mg-10 g per day of L-isovalerylcarnitine are administered.

10. The method of claims 5, wherein 0.01 mg-15 g per day of L-propionylcarnitine are administered.

11. The method of claim 5, wherein 0.1 mg-10 g per day of L-propionylcarnitine are administered.

* * * * *